US007888082B2

(12) United States Patent
Verser et al.

(10) Patent No.: US 7,888,082 B2
(45) Date of Patent: *Feb. 15, 2011

(54) PROCESS FOR PRODUCING ETHANOL FROM CORN DRY MILLING

(75) Inventors: Dan W. Verser, Menlo Park, CA (US); Timothy J. Eggeman, Lakewood, CO (US)

(73) Assignee: Zeachem, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/324,015

(22) Filed: Nov. 26, 2008

(65) Prior Publication Data

US 2009/0081749 A1    Mar. 26, 2009

Related U.S. Application Data

(63) Continuation of application No. 11/339,238, filed on Jan. 24, 2006, now Pat. No. 7,507,562, which is a continuation of application No. 10/268,290, filed on Oct. 9, 2002, now Pat. No. 7,074,603, which is a continuation-in-part of application No. 09/720,930, filed as application No. PCT/US00/06498 on Mar. 10, 2000, now Pat. No. 6,509,180.

(60) Provisional application No. 60/124,276, filed on Mar. 11, 1999, provisional application No. 60/328,258, filed on Oct. 9, 2001.

(51) Int. Cl.
C12P 7/62 (2006.01)
C12P 7/06 (2006.01)

(52) U.S. Cl. .................. 435/135; 435/161; 435/162; 435/165

(58) Field of Classification Search .................. None
See application file for complete search history.

(56) References Cited

U.S. PATENT DOCUMENTS

| | | | |
|---|---|---|---|
| 1,421,605 A | 7/1922 | Steffens |
| 2,079,414 A | 5/1937 | Lazier |
| 2,565,487 A | 8/1951 | Filachione et al. |
| 2,782,243 A | 2/1957 | Hess et al. |
| 3,678,118 A | 7/1972 | Frampton et al. |
| 3,686,334 A | 8/1972 | Britton |
| 3,769,329 A | 10/1973 | Paulik et al. |
| 3,878,261 A | 4/1975 | Gardner |
| 3,956,482 A | 5/1976 | Hahn et al. |
| 4,055,590 A | 10/1977 | Gruber et al. |
| 4,100,189 A | 7/1978 | Mercier |
| 4,113,662 A | 9/1978 | Wall |
| 4,134,926 A | 1/1979 | Tsao et al. |
| 4,140,799 A | 2/1979 | Nagodawithana et al. |
| 4,206,036 A | 6/1980 | Takeuchi et al. |
| 4,275,234 A | 6/1981 | Baniel et al. |
| 4,282,323 A | 8/1981 | Yates |
| 4,353,784 A | 10/1982 | Koga et al. |
| 4,359,404 A | 11/1982 | Grey et al. |
| 4,370,507 A | 1/1983 | Hargis et al. |
| 4,371,619 A | 2/1983 | Schwartz et al. |
| 4,379,028 A | 4/1983 | Berg et al. |
| 4,405,717 A | 9/1983 | Urbas |
| 4,421,939 A | 12/1983 | Kiff et al. |
| 4,431,838 A | 2/1984 | Feldman et al. |
| 4,435,595 A | 3/1984 | Agreda et al. |
| 4,444,881 A | 4/1984 | Urbas |
| 4,454,358 A | 6/1984 | Kummer et al. |
| 4,497,967 A | 2/1985 | Wan |
| 4,506,012 A | 3/1985 | Reed |
| 4,513,084 A | 4/1985 | Keller, Jr. et al. |
| 4,517,391 A | 5/1985 | Ludwig et al. |
| 4,568,644 A | 2/1986 | Wang et al. |
| 4,569,726 A | 2/1986 | Berg et al. |
| 4,636,467 A | 1/1987 | Chynoweth |
| 4,649,112 A | 3/1987 | Datta et al. |
| 4,652,526 A | 3/1987 | Hsu |
| 4,687,668 A | 8/1987 | Ghommidh et al. |
| 4,690,912 A | 9/1987 | Paulik et al. |
| 4,698,303 A | 10/1987 | Bailey et al. |
| 4,771,001 A | 9/1988 | Bailey et al. |
| 4,808,526 A | 2/1989 | Lawford |

(Continued)

FOREIGN PATENT DOCUMENTS

GB      933714      8/1963

(Continued)

OTHER PUBLICATIONS

U.S. Appl. No. 12/511,526, Verser et al. (Jul. 29, 2009).

(Continued)

Primary Examiner—Herbert J. Lilling
(74) Attorney, Agent, or Firm—Sheridan Ross P.C.

(57) ABSTRACT

A process for producing ethanol by the conversion of carbohydrates from a corn dry milling process in which the bottoms fraction from distillation of ethanol in a conventional yeast fermentation is used in a process including a combination of biochemical and synthetic conversions. The process results in high yield ethanol production with concurrent production of high value coproducts. An acetic acid intermediate is produced from bottoms fraction, followed by conversion of the acetic acid into ethanol using esterification and hydrogenation reactions. Coproducts of the process include a high protein content solids fraction produced in the fermentation.

22 Claims, 5 Drawing Sheets

U.S. PATENT DOCUMENTS

| | | | |
|---|---|---|---|
| 4,830,963 | A | 5/1989 | Brumm et al. |
| 4,851,344 | A | 7/1989 | Simon et al. |
| 4,876,196 | A | 10/1989 | Salzbrunn et al. |
| 4,935,360 | A | 6/1990 | Klemps et al. |
| 4,939,294 | A | 7/1990 | Agreda et al. |
| 4,980,164 | A | 12/1990 | Manfredi et al. |
| 5,028,539 | A | 7/1991 | Ingram et al. |
| 5,068,188 | A | 11/1991 | Wise et al. |
| 5,071,754 | A | 12/1991 | Walkup et al. |
| 5,093,121 | A | 3/1992 | Kvanta et al. |
| 5,137,818 | A | 8/1992 | Harder et al. |
| 5,162,214 | A | 11/1992 | Hubred |
| 5,173,429 | A | 12/1992 | Gaddy et al. |
| 5,182,199 | A | 1/1993 | Hartley |
| 5,210,296 | A | 5/1993 | Cockrem et al. |
| 5,231,017 | A | 7/1993 | Lantero et al. |
| 5,254,465 | A | 10/1993 | Wise |
| 5,308,619 | A | 5/1994 | Schmeider et al. |
| 5,316,928 | A | 5/1994 | Flickinger et al. |
| 5,412,126 | A | 5/1995 | King et al. |
| 5,424,202 | A | 6/1995 | Ingram et al. |
| 5,453,365 | A | 9/1995 | Sterzel et al. |
| 5,510,526 | A | 4/1996 | Baniel et al. |
| 5,563,069 | A | 10/1996 | Yang |
| 5,591,877 | A | 1/1997 | Obermeier et al. |
| 5,599,976 | A | 2/1997 | Scates et al. |
| 5,620,877 | A | 4/1997 | Farone et al. |
| 5,681,728 | A | 10/1997 | Miao |
| 5,693,296 | A | 12/1997 | Holtzapple et al. |
| 5,723,639 | A | 3/1998 | Datta et al. |
| 5,750,732 | A | 5/1998 | Verser et al. |
| 5,753,474 | A | 5/1998 | Ramey |
| 5,766,439 | A | 6/1998 | Eyal et al. |
| 5,773,653 | A | 6/1998 | Baniel |
| 5,780,276 | A | 7/1998 | Baniel |
| 5,865,898 | A | 2/1999 | Holtzapple et al. |
| 5,874,263 | A | 2/1999 | Holtzapple et al. |
| 5,892,102 | A | 4/1999 | Mikami et al. |
| 5,969,189 | A | 10/1999 | Holtzapple et al. |
| 5,986,133 | A | 11/1999 | Holtzapple et al. |
| 6,043,392 | A | 3/2000 | Holtzapple et al. |
| 6,136,577 | A | 10/2000 | Gaddy |
| 6,160,173 | A | 12/2000 | Eyal et al. |
| 6,262,313 | B1 | 7/2001 | Holtzapple et al. |
| 6,284,904 | B1 | 9/2001 | Ponnampalam |
| 6,368,819 | B1 | 4/2002 | Gaddy et al. |
| 6,395,926 | B1 | 5/2002 | Holtzapple et al. |
| 6,478,965 | B1 | 11/2002 | Holtzapple et al. |
| 6,509,180 | B1 | 1/2003 | Verser et al. |
| 6,703,227 | B2 | 3/2004 | Jakel et al. |
| 6,740,508 | B2 | 5/2004 | Ulrich et al. |
| 6,926,810 | B2 | 8/2005 | Cockrem et al. |
| 6,927,048 | B2 | 8/2005 | Verser et al. |
| 7,074,603 | B2 | 7/2006 | Verser et al. |
| 7,351,559 | B2 | 4/2008 | Verser et al. |
| 7,494,675 | B2 * | 2/2009 | Abbas et al. .................. 426/12 |
| 7,507,562 | B2 * | 3/2009 | Verser et al. ................. 435/135 |
| 7,601,865 | B2 | 10/2009 | Verser et al. |
| 7,682,812 | B2 | 3/2010 | Verser et al. |
| 2004/0168960 | A1 | 9/2004 | Holtzapple et al. |
| 2004/0171136 | A1 | 9/2004 | Holtzapple et al. |
| 2005/0112739 | A1 | 5/2005 | Golubkov |
| 2006/0024801 | A1 | 2/2006 | Holtzapple et al. |
| 2006/0188980 | A1 | 8/2006 | Holtzapple et al. |
| 2006/0222585 | A1 | 10/2006 | Verser et al. |
| 2007/0014895 | A1 | 1/2007 | Holtzapple et al. |
| 2008/0102502 | A1 | 5/2008 | Foody et al. |
| 2008/0176301 | A1 | 7/2008 | Granda et al. |
| 2008/0193989 | A1 | 8/2008 | Verser et al. |
| 2008/0248540 | A1 | 10/2008 | Yang |
| 2008/0280338 | A1 | 11/2008 | Hall et al. |
| 2009/0203098 | A1 | 8/2009 | Verser |
| 2009/0281354 | A1 | 11/2009 | Mariansky et al. |

FOREIGN PATENT DOCUMENTS

| | | |
|---|---|---|
| JP | S57-140732 | 8/1982 |
| JP | S59-29633 | 2/1984 |
| JP | S61-007222 | 1/1986 |
| JP | S62-171689 | 7/1987 |
| JP | 11-503514 | 3/1999 |
| WO | WO 82/03854 | 11/1982 |
| WO | WO 83/03409 | 10/1983 |
| WO | WO 93/00440 | 1/1993 |
| WO | WO 99/00352 | 1/1999 |
| WO | WO 99/00512 | 1/1999 |
| WO | WO 00/53791 | 9/2000 |
| WO | WO 2004/041995 | 5/2004 |
| WO | WO 2006/007406 | 1/2006 |
| WO | WO 2007/009085 | 1/2007 |
| WO | WO 2008/070561 | 6/2008 |

OTHER PUBLICATIONS

U.S. Appl. No. 12/548,312, Verser et al. (Aug. 26, 2009).
U.S. Appl. No. 12/693,533, Verser et al. (Jan. 26, 2010).
"A Renewed Boost for Ethanol", Chemical Engineering, Feb. 1999, p. 35-39.
Agreda et al., Chem. Eng. Prog., "High Purity Methyl Acetate by Reactive Distillation", pp. 40-46, Feb. 1990.
Balasubramanian, N., Kim, J.S., Lee, Y.Y., "Fermentation of Xylose into Acetic Acid by *Clostridium thermoaceticum*", Appl Biochem and Biotech, vol. 91-93, p. 367-376, 2001.
Ben-Bassat et al., "Ethanol production by thermophilic bacteria: metabolic control of end product formation in *Thermoanaerobium brockii*", J Bacteriol Apr. 1981, 146:1, p. 192-9 (Abstract only).
Bock et al., Biotechnol. Appl. Biochem., "Development of a Low-Cost, Industrially Suitable Medium for the Production of Acetic Acid From Clostridum Thermoaceticum", vol. 25, pp. 117-125 (1997).
Borden, J.R., Lee, Y.Y., Yoon, H.H., "Simultaneous Saccharification and Fermentation of Cellulosic Biomass to Acetic Acid", Appl Biochem and Biotech, vol. 84-86, p. 963-970, 2000.
Brownell, J., Nakas, J., "Bioconversion of Acid-Hydrolyzed Poplar Hemicellulose to Acetic Acid by *Clostridium thermoaceticum*", J. Ind. Microbiol, vol. 7, p. 1-6, 1991.
Busche et al., Biotechnol. Bioeng. Symp., "Recovery of Acetic Acid From Dilute Acetate Solution", No. 12, pp. 249-262 (1982).
Busche, Robert M., Recovering Chemical Products from Dilute Fermentation Broths, Biotechnology and Bioengineering Symp. No. 13, 597-615 (1983).
Buschhorn, H., et al., "Production and utilization of ethanol by the homoacetogen *Acetobacterium woodii*," Appl. Environ. Microbiol. 55, 1835-1840 (1989).
Chang, V.S., Holtzapple, M.T., "Fundamental Factors Affecting Biomass Enzymatic Reactivity", Appl. Biochem. and Biotech., vol. 84-86, p. 5-37, 2000.
Daniel SL, Keith ES, Yang H, Lin YS, Drake HL. Utilization of methoxylated aromatic compounds by the acetogen *Clostridium thermoaceticum*: expression and specificity of the co-dependent O-demethylating activity. Biochem Biophys Res Commun. Oct. 15, 1991;180(1):416-422.
Drake, "Acetogenesis, Acetogenic Bacteria, and the Acetyl-CoA 'Wood/Ljungdahl' Pathway: Past and Current Perspectives", Acetogenesis, 1994, Chapter 1, pp. 3-60, Chapman and Hall, Inc., New York, NY.
Drake, Acetogenesis, Figure 12.2, 1994, p. 343, Chapman Hall, New York.
Drake, et al, "Old Acetogens, New Light" Ann. NY Acad. Sci. 1125: 100-128 (2008).
Eggeman et al. "Recovery of Organic Acids from Fermentation Broths", Mar. 1, 2005, Applied Biochemistry and Biotechnology, vol. 122, pp. 605-618.

Eggeman Tim et al: "The importance of utility systems in today's biorefineries and a vision for tomorrow" Applied Biochemistry and Biotechnology, vol. 130, No. 1-3, Mar. 2006, pp. 361-381, XP002499935 ISSN: 0273-2289.

Filachione et al., Preparation of Esters by Reaction of Ammonium Salts with Alcohols, 5265-5267 (Nov. 1951) [Presented in part at the 116th A.C.S. Meeting held in Atlantic City, N.J., Sep. 1949, and also at the Miniature meeting of the Philadelphia Section of the American Chemical Society held in Philadelphia, PA., in Jan. 1949.].

Grohmann et al., Process Biochem., "Saccharification of Corn Fibre by Combined Treatment with Dilute Sulphuric Acid and Enzymes", vol. 32, No. 5, pp. 405-415 (1997).

Gulati et al. "Assessment of Ethanol Production Options For Corn Products", Bioresource Technology 58, 1996, p. 253-264.

Hull, S.R., Yang, B.Y., Venzke, D., Kulhavy, K., Montgomery, R., "Composition of Corn Steep Water During Steeping", J. Agric. Food Chem., vol. 44, p. 1857-1863, 1996.

Husson et al., Regeneration of Lactic and Succinic Acid-Laden Basic Sorbents by Leaching with a Volatile Base in an Organic Solvent, Ind. Eng. Chem. Res. 37:2996-3005 (1998).

Karnholz, A., Kusel, K., Grossner, A., Schramm, A., Drake, H.L., "Tolerance and Metabolic Response of Acetogenic Bacterial Toward Oxygen", Applied and Environmental Microbiology, vol. 68, No. 2, p. 1005-1009, 2002.

Leathers et al., "Saccharification of Corn Fiber Using Enzymes from *Aureobasidium* sp. Strain NRRL Y-2311-1", Applied Biochemistry and Biotechnology, vol. 59, 1996, p. 337-347.

Liden et al., Two amperometric biosensors as liquid chromatographic detectors for on-line monitoring of carbohydrate consumption and ethanol production in bioprocesses, 8th International Conference on Solid-State Sensors and Actuators, and Eurosensors IX, Stockholm, Sweden, Jun. 1996, vol. 1:474-477.

Lovitt et al., "Ethanol production by thermophilic bacteria: biochemical basis for ethanol and hydrogen tolerance in *Clostridium thermohydrosulfuricum*" J Bacteriol Jun. 1988, 170:6, p. 2809-2815 (Abstract only).

Luedeking et al., J. Biochem. Microbiol. Tech. Eng., "A Kinetic Study of the Lactic Acid Fermentation; Batch Process at Controlled PH", Robert Luedeking & Edgar L. Piret, vol. 1, No. 1, pp. 393-412, 1959.

Lundie (Jr.), L.L., Drake, H.L, "Development of a Minimally Defined Medium for the Acetogen *Clostridium thermoaceticum*", J. of Bacteriology, vol. 159, No. 2, p. 700-703, 1984.

Luo et al., "Kinetics of Simultaneous Saccharification and Lactic Acid Fermentation Processes", Biotechnol. Prog. 1997, 13, 762-767.

Matar et al. "Chemistry of Petrochemical Processes", Gulf Publishing Company, 1994, cover, contents, p. 162-163.

McCoy "Biomass Ethanol Inches Forward", C&EN, Dec. 7, 1998, p. 29-32.

Miller, Richard W. et al: "Extraction of Lactic Acid from a Calcium Lactate Solution Using Amine-Containing Solvents and Carbon Dioxide Gas. 1. Experimental Procedures" Industrial & Engineering Chemistry Research, 35(4), 1156-62, 1996.

Othmer, "Acetic Acid Recovery Methods", Chemical Engineering Progress, Jul. 1958, pp. 48-59, vol. 54, No. 7.

Parekh et al., Acetate Production from Glucose by *Clostridium Thermoaceticum*, Process Biochemistry International, 117-121 (Aug. 1990).

Pöpken, et al., "Reaction Kinetics and Chemical Equilibrium of Homogeneously and Heterogeneously Catalyzed Acetic Acid Esterification with Methanol and Methyl Acetate Hydrolysis", Industrial and Engineering Chemistry Research, Jun. 17, 2000, pp. 2601-2611, vol. 39, No. 7.

Reisinger et al., Extraction and Sorption of Acetic Acid at pH above pKa to Form Calcium Magnesium Acetate, Ind. Eng. Chem. Res., 34:845-852 (1995).

Richert et al., "Thermophilic Fermentation to Make Ethanol from Carbohydrate Byproducts", Genetic Engineering News, Oct. 1, 1998, 1 page.

Ricker et al., Solvent Extraction With Amines for Recovery of Acetic Acid From Dilute Aqueous Industrial Streams, J. Separ. Proc. Technol., 1(2):23-30 (1980).

Ricker, et al., "Solvent Properties of Organic Bases for Extraction of Acetic Acid from Water", Journal of Separation Process Technology, 1979, pp. 36-41, vol. 1, No. 1.

Saha, et al., "Recovery of dilute acetic acid through esterification in a reactive distillation column", Catalysis Today, 2000, pp. 147-157, vol. 60.

Savage, M.D., Drake, H.L., "Adaptation of the Acetogen *Clostridium thermoautotropicum* to Minimal Medium", Journal of Bacteriology, vol. 165, No. 1, p. 315-318, 1986.

Schwartz, et al., "Acetic Acid Production by *Clostridium thermoaceticum* in pH-Controlled Batch Fermentations at Acidic pH", Applied and Environmental Microbiology, Jun. 1982, pp. 1385-1392, vol. 43, No. 6.

Schwartz, R.D., Keller Jr., F.A., "Isolation of a Strain of *Clostridium thermoaceticum* Capable of Growth and Acetic Acid Production at pH 4.5", Applied and Environmental Microbiology, vol. 43, No. 1, p. 117-123, 1982.

Tamada et al., Extraction of Carboxylic Acids with Amine Extractants. 3. Effect of Temperature, Water Coextraction, and Process Considerations, Ind. Eng. Chem. Res. 29:1333-1338 (1990).

Tang et al., Appl. Microbiol. Biotechnol., "Acetic Acid Production From Whey Lactose by the Co-Culture of *Sterpococcus Lactis* and *Clostridium Formicoaceticum*", 28:138-143 (1988).

Wang et al., Biochem. Eng. Renewable Sources, "A Novel Route to the Production of Acetic Acid by Fermentation", No. 181, vol. 74, pp. 105-110 (1978).

Wardell et al., Solvent Equilibria for Extraction of Carboxylic Acids from Water, Journal of Chemical and Engineering Data, 23(2):144-148 (1978).

Witjitra, K., Shah, M.M., Cheryan, M., "Effect of Nutrient Sources on Growth and Acetate Production by *Clostridium thermoaceticum*", Enzyme and Microbial Technology, vol. 19, p. 322-327, 1996.

Xin et al. "Recovery of acetic acid from waste water", Chemical Engineering (China), vol. 24, No. 5, pp. 41-44 (including translated abstract) Pub Date Oct. 25, 1996.

Xu et al., Canadian J. Chem. Eng., "Kinetics of Acetic Acid Esterification Over Ion Exchange Catalysts", vol. 74, pp. 493-500, Aug. 1996.

Yang et al., Biotechnol. Bioeng., "Kinetics and Mathematical Modeling of Homoacetic Fermentation of Lactate by *Clostridium Formicoaceticum*", vol. 32, pp. 797-802 (1988).

Zeikus et al., "Thermophilic Ethanol Fermentations", Basic Life Sci, 1981, vol. 18, p. 441-61 (Abstract only).

Zhicai et al., Esterification—Distillation of Butanol and Acetic Acid, Chemical Engineering Science, 53(11):2081-2088 (1998).

\* cited by examiner

US 7,888,082 B2

PROCESS FOR PRODUCING ETHANOL FROM CORN DRY MILLING

CROSS-REFERENCE TO RELATED APPLICATIONS

This application is a continuation of U.S. patent application Ser. No. 11/339,238 filed Jan. 24, 2006 (now U.S. Pat. No. 7,507,562, issued Mar. 24, 2009), which is a continuation of U.S. patent application Ser. No. 10/268,290, filed Oct. 9, 2002 (now U.S. Pat. No. 7,074,603 issued Jul. 11, 2006), which is a continuation-in-part of U.S. patent application Ser. No. 09/720,930, filed Dec. 29, 2000 (now U.S. Pat. No. 6,509,180 issued Jan. 21, 2003), which was filed as an application under 35 U.S.C. 371 based on PCT Application No. PCT/US00/06498, filed Mar. 10, 2000. PCT Application No. PCT/US00/06498 claims the benefit of priority under 35 U.S.C. 119(e) from U.S. Provisional Patent Application No. 60/124,276, filed on Mar. 11, 1999. Said U.S. patent application Ser. No. 10/268,290 (issued U.S. Pat. No. 7,074,603) also claims priority under 35 U.S.C. 119(e) from U.S. Provisional Patent Application No. 60/328,258, filed on Oct. 9, 2001. All of the foregoing applications are incorporated in their entirety by reference.

FIELD OF THE INVENTION

This invention relates to a process for the conversion of the unfermented fraction of the corn from a conventional yeast fermentation based corn dry milling ethanol process into ethyl acetate or ethanol for fuel or chemical use. The invention uses a combination of fermentation and chemical conversion to greatly increase the yield of ethanol from carbohydrates compared to the current art.

BACKGROUND OF THE INVENTION

The United States is the world's largest producer of corn. US production reached 9.5 billion bushels in 2001, greatly exceeding the production of any other grain (National Corn Growers Association 2002). Direct use as animal feed is the largest consuming application, accounting for 5.85 billion bushels in 2001. Corn processing, either via wet milling into sweeteners, starch, ethanol and other industrial products, or via dry milling for ethanol production, accounted for 1.7 billion bushels of US consumption in 2001, or slightly less than 18% of the crop.

Corn processing is expected to increase significantly over the next decade. Ethanol production has been the largest single application of corn processing since 1999, reflecting the recent high growth of the fuel ethanol market and the slowing growth of sweetener markets. Legislative and lobbying efforts are promoting a renewable fuels standard for gasoline. Most projections are for a three fold increase in ethanol production, accounting for another 1.4 billion bushels of corn consumption if no significant changes are made to existing manufacturing processes. Other new industrial uses for corn, such as biodegradable plastics, will also contribute to the expansion of the corn processing industry.

A conventional corn dry milling process with the production of ethanol is illustrated in FIG. 1. Briefly, the process involves an initial preparation step of grinding and cooking the corn 110. The resulting product is subjected to a step of hydrolysis 120. Then a yeast fermentation is conducted for the production of ethanol 130. The ethanol is distilled from the fermentation broth 140 and dried 150. The remainder of the fermentation medium is then dried to produce DDGS 160. This step typically includes a solid/liquid separation 170, wherein the liquid stream is subjected to an evaporation step 180 to concentrate soluble byproducts, such as sugars, glycerol and amino acids, before being recombined with the solids to be dried into DDGS.

The economics of corn processing are dependent to a great degree on the value of the animal feed coproducts made from the non-starch fractions of corn. The projected expansion of the industry will likely result in severe oversupply conditions in the coproduct markets unless changes are made. In particular with the expansion of the dry mill ethanol industry there will be a huge increase in supply of distiller's dried grains and solubles (DDGS). There are several limitations on the utilization of DDGS, including limited export markets which are hampered by continuing disputes with trading partners, and the limited market range in terms of animal feeding systems, essentially limited to ruminants.

It would be desirable to increase the value of the coproducts and to expand the range of markets beyond ruminant animals. One way to do this is to utilize the fiber fraction of the corn. Various schemes have been derived to hydrolyze the fiber fraction of the corn for utilization as a fermentation substrate. However the fiber fraction is complex and is composed of hemicellulose and cellulose components and yields a hydrolysate, upon enzymatic hydrolysis, for example, that is of limited use as a substrate in the conventional yeast based ethanol process. Thus it would be desirable to have a process that could utilize the complex mixture of components from corn fiber hydrolysate. It would also be desirable to utilize the metabolic byproducts from the yeast fermentation such as glycerol which is a difficult material to handle in the ethanol plant particularly in drying of DDGS. If the fiber fraction of the corn could be utilized it would increase the yield from the plant and concentrate and thus increase the value of the corn protein fraction of the corn. The increased concentration of protein with lower fiber content is a higher value animal feed coproduct. For example, corn gluten meal is a fraction of corn protein produced in corn wet milling that has low fiber content, a higher protein concentration than DDGS, contains the pigments from the corn, and has a market value of greater than twice DDGS. Corn gluten meal can also be utilized in a broader range of markets than DDGS such as chickens and other monogastric animals. By selectively removing the fiber fraction from DDGS, a product more like corn gluten meal would be produced with higher value.

In addition, since there are a large number of already existing ethanol plants based on corn dry milling, and the number is increasing rapidly, it would be desirable to have a process that could be integrated with these plants to improve the product value, increase yield and utilize to the greatest extent possible the existing physical plant assets.

Thus, a need exists for improvements in the corn dry milling process to increase ethanol production and to develop byproducts of higher value and with broader markets than DDGS.

SUMMARY OF THE INVENTION

The present invention is an integrated ethanol production process that can be conducted in most conventional ethanol production facilities based on dry corn milling. The process is for the production of ethanol from corn. The process includes conducting a yeast fermentation in a corn preparation to produce ethanol. The ethanol is distilled from the yeast fermentation to produce a bottoms fraction, which is then hydrolyzed. In one embodiment, the bottoms fraction can be contacted with a protease. The hydrolyzed bottoms fraction is separated into a solids fraction and a liquid hydrolyzate. The liquid hydrolyzate is used as a medium for culturing a homofermentative microorganism to produce acetate and/or acetic acid. The process further includes chemically converting the acetate and/or acetic acid to an ester of acetic acid, which can be ethyl acetate. In an alternative embodiment, the acetate and/or acetic acid is chemically converted to ethanol. In one embodiment of the invention, the step of hydrolyzing can include hot water pretreatment and/or enzymatic hydrolysis (such as by contacting the bottoms fraction with xylanase and cellulase enzymes) of the bottoms fraction. In another embodiment, the fermentable fraction of the liquid hydrolysate is less than about 6% by weight.

In a further embodiment, the solids fraction comprises a majority of the protein from the corn, and the protein content can be at least about 35% protein on a dry weight basis. The solids fraction also includes the lipid fraction from the corn. Typically, the volume of the solids fraction is about one-half the volume of distiller's dried grains and solubles (DDGS) produced by the same volume of corn preparation. The solids fraction can also be dried and in particular, the step of drying is conducted with a dryer suitable for producing DDGS from a bottoms fraction. The step of drying can be conducted without a pre-step of separating and concentrating a liquid portion of the solids fraction.

In the process of the present invention, the homofermentative microorganism can be a homoacetogenic microorganism, such as a microorganism is of the species *Clostridium thermoaceticum* or *Clostridium formicoaceticum*. Also, the step of culturing can include converting by fermentation the liquid hydrolyzate into lactic acid and/or lactate, such as by a homolactic fermentation, and converting by fermentation the lactic acid and/or lactate into acetic acid and/or acetate, such as by a homoacetic fermentation.

In a further embodiment, the step of chemically converting the acetate and/or acetic acid to an ester of acetic acid can include (i) esterifying the acetic acid to an acetic acid ester in the presence of an alcohol, and (ii) hydrogenating the acetic acid ester to ethanol and the alcohol. The alcohol produced in step (ii) can be recycled to step (i). Alternatively, the alcohol in step (i) can be ethanol produced by the yeast fermentation.

In another embodiment, the process can include acidifying the acetate with carbon dioxide to produce acetic acid and calcium carbonate; esterifying the acetic acid with an alcohol to form an ester; and recovering the ester. Further, the ester can be recovered by distillation, such as reactive distillation capable of pushing the acidification and esterification equilibria to high conversion to the desired ester product. Further, the ester can be converted to ethanol.

BRIEF DESSCRIPTION OF THE DRAWINGS

DETAILED DESCSCRIPTION OF THE INVENTION

Figure 1:
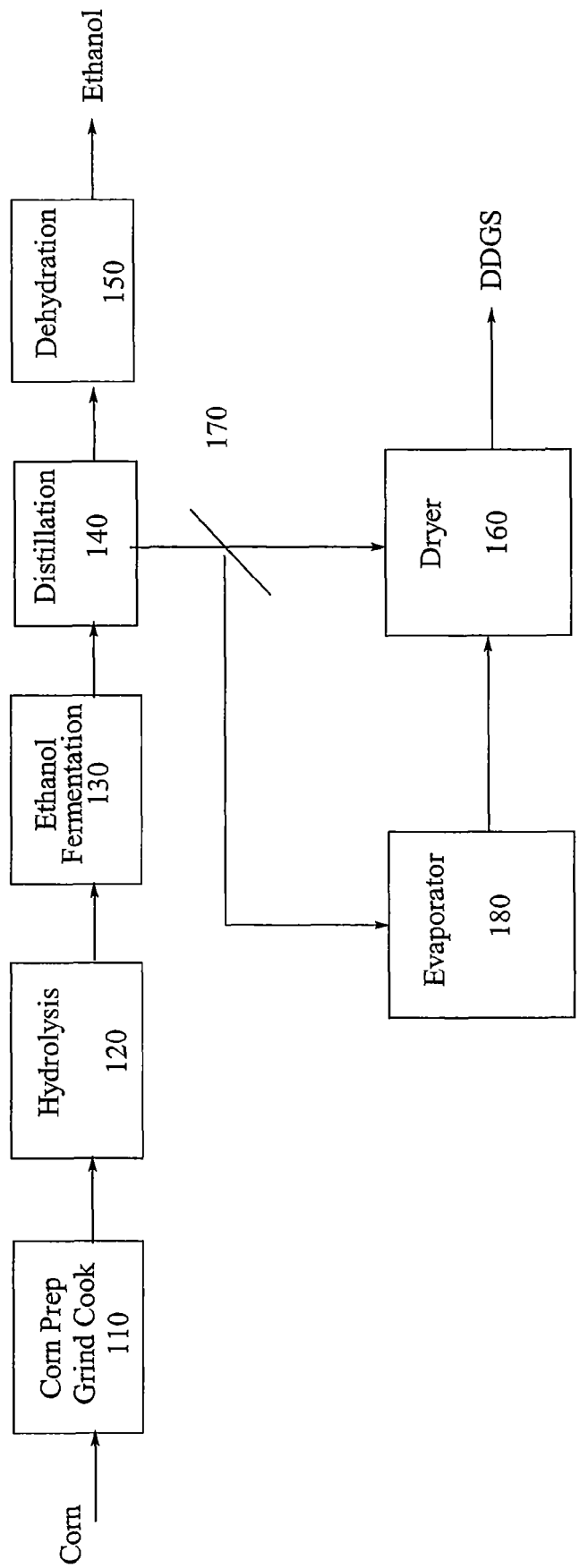
FIG. 1 is a block diagram a prior art process for the production of ethanol based on corn dry milling.

One embodiment of the process of the present invention is a unique process for the production of ethanol based on dry milling of corn. A conventional ethanol production process based on the dry milling of corn is shown in FIG. 1. The present invention uses the bottoms fraction from distillation of ethanol in the process as a carbohydrate and nitrogen source in a process that is described in more detail in U.S. patent application Ser. No. 09/720,930 to make an integrated ethanol production process. A key feature of this approach is the production of acetic acid from various sugars using an anaerobic acetogenic bacterium.

Figure 2:
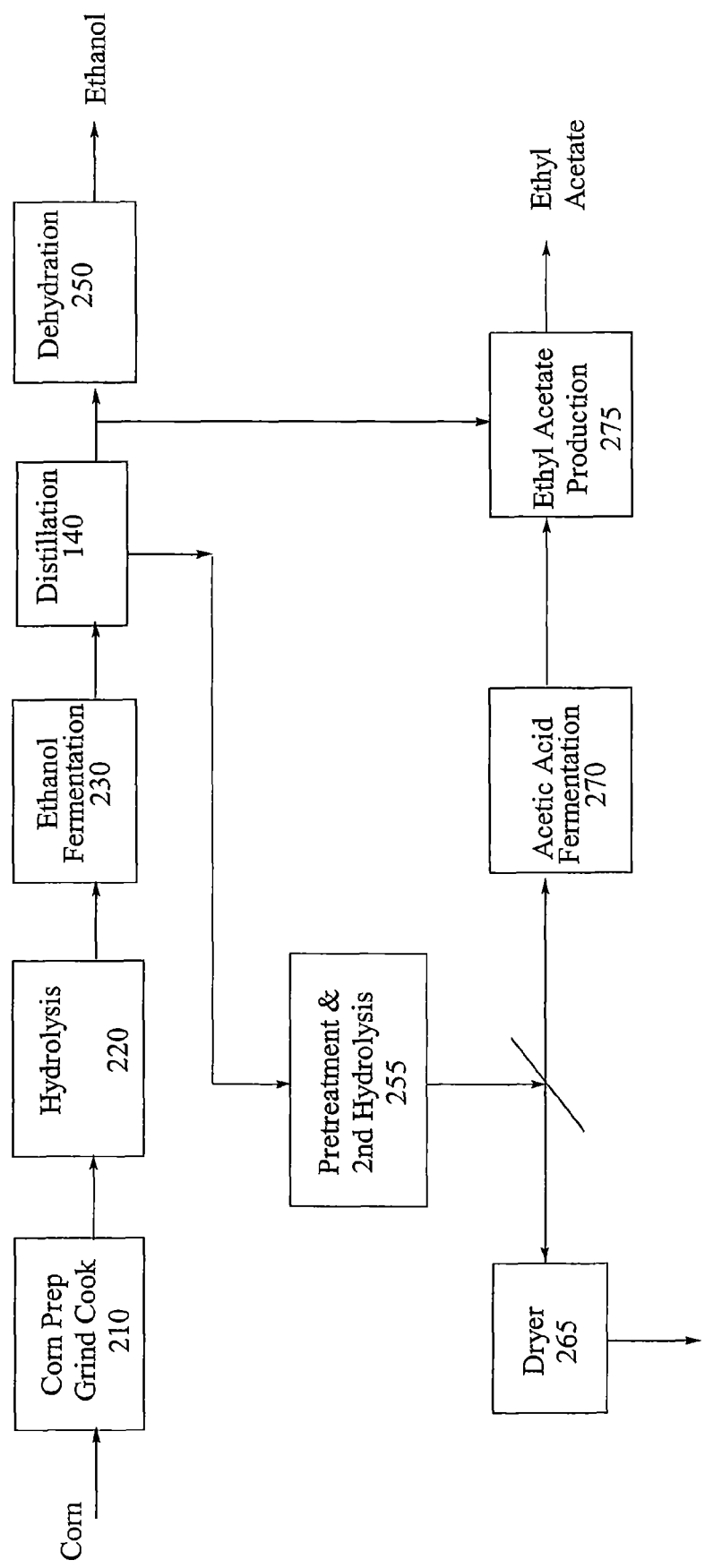
FIG. 2 is a block diagram of on embodiment of the process of the present invention.

A preferred embodiment of the present invention is illustrated in FIG. 2. The conventional steps of corn preparation 210, hydrolysis 220, ethanol fermentation 230, distillation 240, and dehydration 250 are shown. Also shown in FIG. 2 is a bottoms fraction from the distillation is subjected to a pretreatment and second hydrolysis step 255, utilizing cellulase and xylanase enzymes, mainly to hydrolyze the fiber fraction of the bottoms. The resulting hydrolyzate is sent to a solid/liquid separation 260. The solid fraction from the separation is then dried as a high protein byproduct 265. The liquid fraction is used in a fermentation medium, in this particular embodiment, for the production of acetic acid 270. The acetic acid is then converted to ethyl acetate 275.

In an alternative embodiment, the hydrolysis step 255 includes the use of protease enzymes. In this case a majority of the solid fraction of the beer still bottoms stream is converted to soluble components including sugars and amino acids which are used for the production of acetic acid and bacterial SCP as described in more detail in the following.

The chemical product of the fermentation can be used as an intermediate for ethanol production by the following route (illustrated using glucose) as described in more detail in U.S. patent application Ser. No. 09/720,930 to make an integrated ethanol production process:

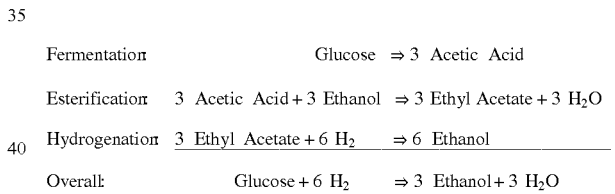

Each step can be done at high yield, so nearly every mole of acetate produced in the fermentation ends up as a mole of ethanol. In other words, each C6 sugar produces 3 moles of ethanol in our indirect route. By comparison, direct fermentation routes only produce 2 moles of ethanol for each C6 sugar. This 50% improvement in sugar utilization has a dramatic effect on the economics of bioethanol production.

Alternatively the process in the current invention can utilize part of the ethanol produced in the conventional ethanol process and produce ethyl acetate as a final product for sale as an additional product from the plant using the esterification process described in more detail in U.S. patent application Ser. No. 09/720,930 to make an integrated ethanol production process.

This integrated process for the production of ethanol by dry milling of corn provides improved fiber utilization, upgrading of coproducts and the production of a higher value new product compared to conventional ethanol production based on the dry milling of corn and utilizes the existing physical assets of the original ethanol production plant to a large extent. There are a number of features of the acetogenic fermentation, which make it particularly suited to corn fiber utilization in a dry mill.

Preparation of Bottoms Fraction as Fermentation Substrate

In a conventional corn dry milling ethanol production process, after the fermentation is conducted, the ethanol is distilled and recovered. The remaining fermentation medium is referred to as a "bottoms fraction" or "beer bottoms." In accordance with the present process, the bottoms fraction is used as a carbohydrate and nitrogen source in the process broadly described in U.S. patent application Ser. No. 09/720,930.

The utilization of corn fiber in the bottoms fraction requires the hydrolysis of the fiber to monomeric sugars. This can be accomplished in two stages, a pretreatment step and an enzymatic hydrolysis step.

The simplest pretreatment approach, and one that is suitable for corn fiber is the use of hot water at a moderately high temperature. Such treatments are well know in the art. For example, see Weil et al., Appl. Biochem. And Biotech., 73:1-17 (1998).

Prior to the pretreatment step, the pH can be adjusted to prevent degradation of the sugars by acid production. For example, the pH can be adjusted to between about 5 and about 7. Any suitable base can be used for pH adjustment, including without limitation potassium hydroxide.

The further hydrolysis of corn fiber after the pretreatment step is preferably an enzymatic hydrolysis step. The enzymatic hydrolysis step can be conducted with a mixture of enzymes in combination, including xylanase and cellulase. There are several reasons why the present process is well suited to enzymatic hydrolysis on an economic basis. The raw material stream required for the acetogenic fermentation is very dilute. This means that the stream subjected to enzymatic hydrolysis can be made very dilute so as not as limited by feedback inhibition. The desired product hydrolysate can be about 3.5% fermentable sugars. The total fermentable fraction of the resulting hydrolyzed bottoms fraction (i.e., carbohydrate plus nitrogen source) is preferably less than about 6% by weight and more preferably less than about 5% by weight. The concentration of the hydrolyzed bottoms fraction can be controlled simply by dilution of bottoms fraction from the yeast fermentation. The acetogenic organisms can also use dimer sugars such as cellobiose. The use of mixtures of enzymes can reduce the total overall loading. The high yield from the raw material in the fermentation reduces the total enzyme cost in terms of cost per unit of product.

The resulting hydrolyzed bottoms fraction is then subjected to a solid/liquid separation and the liquid fraction (i.e., liquid hydrolysate) is used as a substrate in a subsequent fermentation, as described below. The solids fraction is typically dried and can be dried with the same type of drier that is used to dry DDGS, thereby utilizing equipment from existing corn dry milling ethanol production facilities. The solids fraction from the hydrolyzed bottoms fraction is a high protein byproduct that includes the majority of the protein and the lipid fraction from the corn. DDGS typically has a protein content of about 28% by weight on a dry weight basis. By contrast, the high protein byproduct of the present invention has a protein of at least about 35% by weight, more preferably at least about 45% by weight and more preferably at least about 50% by weight. The dried solids fraction of the present invention, while significantly higher in protein content is typically about one-half the volume of DDGS prepared from the same volume of corn preparation.

In an alternative embodiment, the protein fraction of the corn in the bottoms fraction is hydrolyzed to amino acids and small peptides by protease enzymes. This protein content thereby becomes available for conversion to bacterial single cell protein (SCP) in subsequent fermentation. SCP has a better amino acid profile that the original corn proteins since the bacteria can produce essential amino acids they need from the amino acids in the corn. The amino acid profile of bacterial SCP allows the marketing of the coproduct into an even wider range of markets that corn gluten meal, including carnivorous fish, for example. Thus this alternative embodiment reforms the protein content of the corn into a higher value SCP. In this alternative process in which SCP is produced, a protease enzyme is utilized in addition to the xylanase and cellulase enzymes during hydrolysis.

The invention involves the use of acetogenic bacteria. This class of bacteria was first isolated in the 1930's and it is a group of obligate anaerobic bacteria that can use the acetyl-CoA pathway to fix carbon dioxide, resulting in the reductive synthesis of acetic acid or the incorporation of carbon dioxide into cellular materials via acetyl-CoA. Habitats of these bacteria are sewers, sediments, termite guts, rumens, and the intestinal tracts of monogastrics including humans. Pathogenicity is rare.

The acetogenic bacteria include members in the *Clostridium, Acetobacterium, Peptostreptococcus, Sporomusa* and a couple of other lesser known species. Acetogens can be further characterized as being either homoacetogens or heteroacetogens depending upon whether acetic acid is the only major metabolic product. By far the most work to date has been done with *C. thermoaceticum. C. thermoaceticum* is a gram variable, spore forming, thermophilic homoacetogen originally isolated from horse manure.

These organisms metabolize glucose to pyruvate using the Embden-Meyerhof glycolytic pathway. Lactic acid is also metabolized by first converting it back to pyruvate.

Pyruvate is decarboxylated and then oxidized to acetate with the concurrent production of ATP. The main distinguishing feature of acetogenic bacteria is that the $CO_2$ produced in the decarboxylation step is not released to the environment. Instead, the acetyl-CoA pathway is used to fix the $CO_2$ and make an additional mole of acetic acid. Thus, for glucose fermentation the overall stoichiometry is:

Glucose 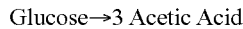 3 Acetic Acid

Two of the acetic acid molecules are made from oxidation of glucose, the third is made by the reduction of the carbon dioxide byproduct of glucose oxidation. Ignoring the effects of cell mass production, the homoacetogens are capable of converting glucose into acetic acid at 100% theoretical mass yield.

A very important feature is the ability of the organisms to use a very wide range of raw material substrates. These include materials with a wide range of carbon numbers.

Five carbon sugars like xylose, a major monomer of hemicellulose, are converted to fructose-6-phosphate and glyceraldehyde-3-phosphate via the pentose phosphate pathway. Both of these intermediates are then passed to glycolysis to produce pyruvate, followed by conversion of pyruvate to acetate using the oxidative and acetyl-CoA pathways. While not reflective of the elementary reactions involved, the overall stoichiometry for xylose fermentation by acetogens is:

2 Xylose 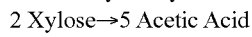 5 Acetic Acid thus homoacetogens are also capable of converting xylose into acetic acid at near 100% theoretical mass yield. This an important feature since current R&D efforts for improving the value of fiber are focused on hydrolysis of the cellulose and hemicellulose into a mixture of five and six carbon sugars. The natural ability of the acetogens to metabolize both five and six carbon sugars provides a distinct advantage over other strains considered for fermenting fiber hydrolyzates.

Overall the organisms can utilize a wide range of substrates (Drake, 1994), including:
C3: glycerol, lactate
C5: xylose
C6: glucose, fructose
C12: sucrose, lactose, cellobiose, maltose In addition, the organisms can utilize and tolerate acids, alcohols and aromatic monomers from the breakdown of lignin in biomass. These combined features allow the organisms to utilize very complex raw materials from the hydrolysis of cellulosic material from corn fiber, corn stover (stalks), or other biomass. Often the complete hydrolysis of cellulosic biomass, including corn fiber, combines acid hydrolysis with enzymatic hydrolysis. The breakdown products from acid hydrolysis produce organic acids and aromatic monomers, which are inhibitory to traditional fermentation organisms such as yeast.

Recent efforts have shown that corn steep liquor is a satisfactory low-cost media component that greatly improves cell growth rates (Bock et. al. 1997, Witjitra et. al. 1996, Balasubramanian et. al. 2001).

Several kinetic studies (Yang et. al. 1988, Wang et. al. 1978, Tang et. al. 1988) have been conducted to examine the effects of pH and acetate levels on both cell growth and acid production. Unfortunately the organisms are sensitive to low pH and product inhibition occurs at much lower concentrations than with lactic acid bacteria. Optimal pH is around 7 and maximum acetate tolerance is about 30-50 g/l in batch fermentation There are other useful features of the fermentation from an industrial perspective. The fermentation takes place at a relatively high temperature, e.g. 58° C., thus reducing the possibility of contamination of the fermentation by stray organisms. The fermentation is anaerobic and thus there is no need for gas exchange. This greatly reduces the mixing and gas compression requirement and eliminates another source of possible contamination.

The most important reason that acetogenic fermentations have not been utilized at an industrial scale is the limitation of product concentration in the fermentation broth by product inhibition. Acetic acid and acetate salts are very toxic to the fermentation organisms. At low concentrations, about 3-4%, the product stops the fermentation. Thus the product from the fermentation is a dilute acetate salt solution such as calcium acetate. This limitation is overcome by the reactive separation process described below.

Fermentation Process

The overall purpose of the fermentation part of the current invention is to convert the fermentable carbohydrates and amino acids into acetic acid and single cell bacterial protein. In a preferred embodiment a two step fermentation process is used. The first step uses a homofermentative lactic acid bacteria to convert the bulk of the fermentable sugars into lactic acid and single cell protein. The second step uses a homofermentative acetogenic bacteria to convert lactic acid and residual carbohydrates into acetic acid.

The lactic acid fermentation step uses a homofermentative lactic acid bacteria such as *Lactobacillus casei* to convert the fermentable sugars into lactic acid. Lactic acid bacteria are gram-positive, non-spore forming, aerotolerant anaerobes. These bacterial are found in the mouths and intestinal tracts of most warm blooded animals including humans. None are pathogenic and many are approved by the United States FDA as viable organisms for use in direct-fed microbials for animal feeds. Viable cultures are also present in many yogurts consumed by humans.

Figure 3:
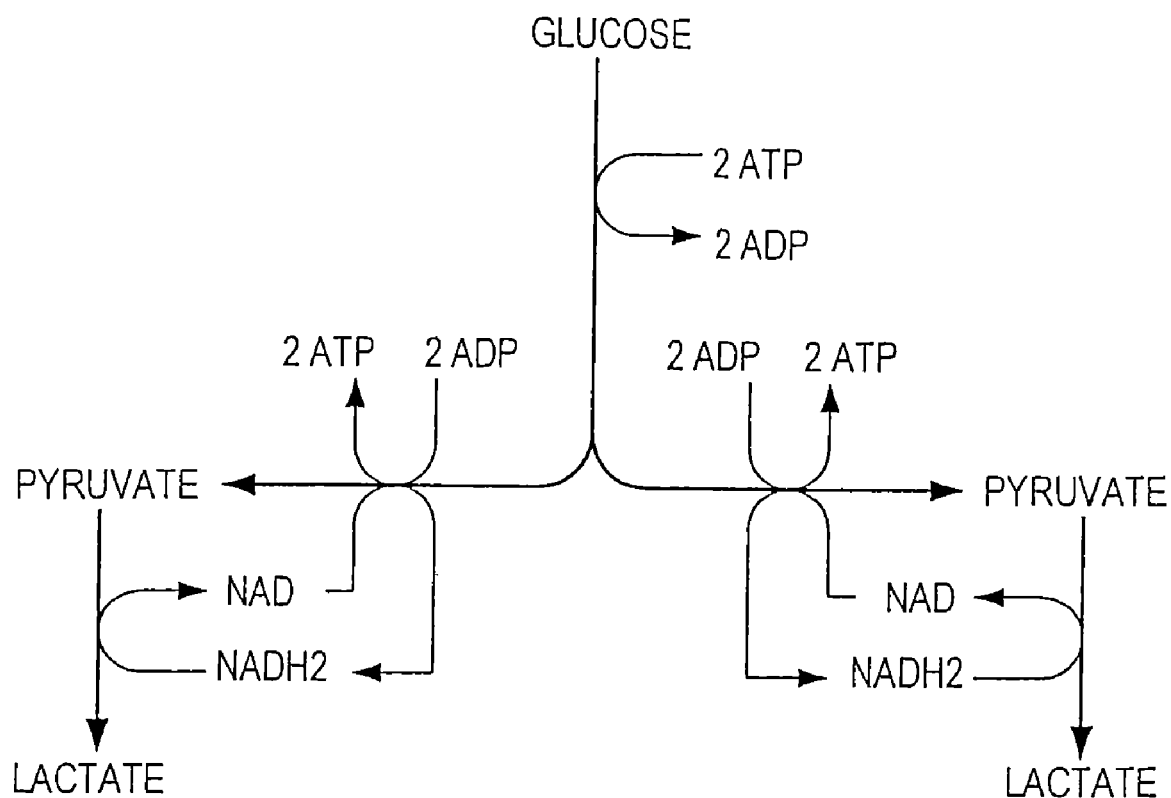
FIG. 3 illustrates the metabolic pathway for the conversion of glucose to lactate.

As shown in FIG. 3, lactic acid is the sole metabolic product for homofermentative strains. Glucose is metabolized to pyruvate using the regular Embden-Meyerhof glycolytic pathway. Pyruvate is converted to lactic acid in a single NAD coupled step. Most lactic acid bacteria are mesophilic with optimal temperatures for growth between 35 to 45 C. Cell growth is pH sensitive with optimal pH around 6.0. Product inhibition begins to affect the kinetics of cell growth and acid production at lactic acid levels above 4 wt %. Complete inhibition of growth occurs around 7 wt % while complete inhibition of acid production occurs around 10-12 wt %.

The feed to the fermentation is very dilute in carbohydrates with only about 5 wt % fermentable sugars. A single stage continuous stirred tank reactor (CSTR) type fermentor is appropriate for this step. However, any suitable bioreactor can be used, including batch, fed-batch, cell recycle and multi-step CSTR. The low carbohydrate concentration in the feed will limit the effects of product inhibition on the cell growth and acid production kinetics, thus 90+% conversion of the dextrose with about 18-24 hour residence times is possible. Most homofermentative strains will readily metabolize a range of substrate sugars. It is advantageous to combine the lactic acid fermentation with the subsequent acetic acid fermentation in such a manner so as to utilize all of the sugars.

In contrast to many industrial lactic acid fermentations, the current invention may be operated in a mode in which the fermentation is carbohydrate limited rather than nitrogen limited. Thus biomass production is maximized by keeping most of the fermentation in the growth associated state and ensuring that sufficient nitrogen is available for growth. For any growth associated fermentation the biomass yields are typically about 10.5 g per mole of ATP produced. Since lactic acid fermentations produce a net of 2 moles of ATP per mole of glucose, the biomass yield will be around 2 (10.5/180)=0.12 g per g of glucose. By stoichiometry, the remaining 0.88 g of glucose are converted into 0.88 grams of lactic acid.

The efficient production of biomass as single cell protein is an important part of this invention. In contrast to the production of single cell protein historically, the use of an anaerobic homofermentative fermentation is very advantageous. This is because all of the energy production of the organism comes from the production of the desired metabolite whether lactic acid or acetic acid. This means that there is no wasted byproduct $CO_2$ as is the case in aerobic fermentations. In addition, because of the lack of production of $CO_2$, the heat produced by the fermentation is also minimized. Therefore the utilization of energy contained in the raw material carbohydrates is maximized toward the production of valuable single cell protein or lactic and acetic acid. The traditional yeast fermentation, in addition to wasting mass as $CO_2$, also requires the removal of heat.

The fermented broth from the first fermentation step is clarified using a centrifuge. The concentrate contains the lactic acid bacteria and is sent to single cell protein recovery. The amount of single cell protein produced is related to the amount of nitrogen in the form of hydrolyzed proteins as amino acid and peptides that is supplied to the fermentation in the medium. This can range from a very small amount, but not zero, as lactic acid bacteria require some complex nitrogen sources, such as 1% up to about 15% overall yield of single cell protein based on the total nitrogen plus carbohydrate in the medium. It is a feature of the invention that the production of single cell protein can be controlled over a wide range. The single cell protein can be processed by any suitable means, such as spray drying, to produce a salable product.

Another important feature of the current invention is the production of a single cell protein which is enhanced in value as an animal feed ingredient. The single cell protein from the lactic acid fermentation has these features. It has a high protein concentration of about 70%, depending on the strain of organism and the specific conditions of the fermentation. It has a good amino acid profile. That is, it contains a high percentage of so called essential amino acids comprising, for example, lysine, methionine, isoleucine, tryptophan, and threonine. The combined percentage of these amino acids in lactic acid bacteria is about 10.5%, compared to corn protein which has about 1% of the total corn kernel. The protein composition of corn depends on the fraction of the corn considered. Corn gluten meal, for example, has about 7.5%, but corn gluten feed has about 2.5% of essential amino acids. This enhanced amino acid composition is directly related to the value of the protein as an animal feed ingredient.

In a preferred embodiment, the current invention can produce single cell protein at high efficiency and with high value. The centrate, from the separation of the lactic acid bacteria from the fermentation broth of the first fermentation, is fed to a second fermentor where the lactate is converted into acetate using an acetogenic bacteria. Lactate can be a preferred substrate for acetogenic bacteria in many of their natural environments. The rate of fermentation and yield on lactate substrate can be very high, e.g., over 98% yield of acetate from lactate.

Incomplete removal of the lactic acid bacteria is typically acceptable since the acetic acid fermentation typically uses a thermophilic strain and the second fermentation is done at a higher temperature. Contamination of the acetic acid fermentation with a mesophilic lactic acid bacteria is typically not an issue since the lactic acid bacteria typically cannot grow at these higher temperatures. Also, near complete conversion of the glucose is expected in the first fermentor, so the lactic acid bacteria which do happen to bleed through the centrifuge into the second fermentor will not have a carbohydrate source.

The acetogenic bacteria have been known and studied since the 1930's. Drake, H. L. (editor), *Acetogenesis,* Chapman & Hall, 1994, gives a good overview of the field. The acetogenic bacteria include members in the *Clostridium, Acetobacterium, Peptostreptococcus* and other lesser known species. The habitats of these bacteria are: sewers, anaerobic digesters at municipal waste treatment plants, natural sediments, termite guts, rumens, and intestinal tracts of non-ruminants including humans. Pathogenicity is rare. All of these organism are strict anaerobes, which means that contact with oxygen is often fatal to the microorganism. *Clostridium* are spore formers. Spores are resistant to many sterilization techniques and special procedures have been established for handling spore-forming bacteria. The *Acetobacterium* and *Peptostreptococcus* species are not spore formers.

Figure 4:
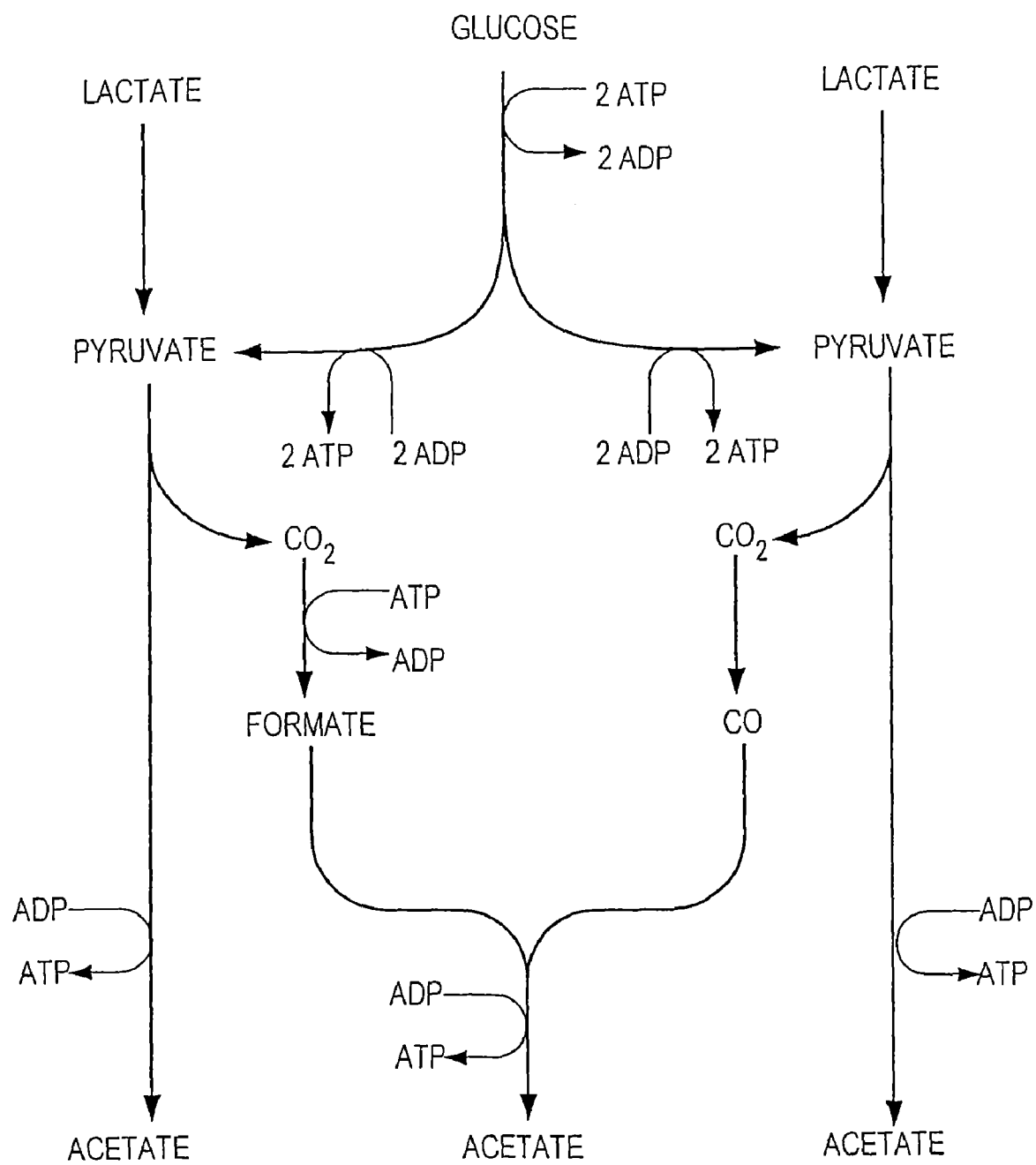
FIG. 4 illustrates the metabolic pathway for the conversion of glucose to acetate.

FIG. 4 is a simplified sketch of the metabolic pathways used by most acetogenic bacteria. The organism metabolizes glucose to pyruvate using the normal Embden-Meyerhof glycolytic pathway. Lactic acid is also metabolized by first converting it back to pyruvate. From pyruvate, the organism makes acetic acid and carbon dioxide using the regular oxidation pathways. The main distinguishing feature of acetogenic bacteria is that the $CO_2$ produced in this oxidation step is not released to the environment. Instead, the acetogenic bacteria have a metabolic pathway which will fix the $CO_2$ and make an additional mole of acetic acid.

The novel acetogenic pathway provides three functions for the organism:

1. Like all anaerobes, a terminal electron acceptor other than oxygen is required to balance the redox reactions of metabolism. In this case, the reduction of carbon dioxide acts as the electron sink.

2. Cellular energy (i.e. ATP) is produced from this pathway. The metabolic pathways for conversion of one mole of glucose into two moles of acetic acid and two moles of carbon dioxide produce four ATP per mole of glucose consumed. Addition of the acetogenic pathways creates another acetic acid molecule from the carbon dioxide and increases the ATP yield to 4 B 6 ATP per mole of glucose. The additional ATP are not made directly from the substrate-level phosporylation but are made in other processes such as the electron transport chain and from ion pumps located in the cell membranes. The exact amount of ATP produced from the secondary sources varies from strain to strain and is also dependent upon the cell environment.

3. Carbon dioxide can be converted into cellular carbon needed for growth using the cell's anabolic pathways, even when common carbon sources such as glucose are not available.

Some acetogens will produce other organic acids such as formic, propionic, succinic, etc. in addition to acetic acid. These organisms are described as heterofermentative as opposed to the homofermentative organisms which only produce acetic acid. The heterofermentative pathways represent a potential yield loss in the current invention, and proper strain selection and elucidation of the factors which cause the formation of these other organic acids will minimize the impact.

By far, most work to date has been with the *Clostridium* strains. Many of these strains are thermophilic with optimal temperatures for growth around 60 C. Several kinetic studies (Yang, S. T., Tang, I. C., Okos, M. R., "Kinetics and Mathematical Modeling of Homoacetic Fermentation of Lactate By *Clostridium formicoaceticum*", Biotechnology and Bioengineering, vol. 32, p. 797-802, 1988, Wang, D. I., Fleishchaker, R. J.; Wang, G. Y., "A Novel Route to the Production of Acetic Acid By Fermentation", AIChE Symposium Series-Biochemical Engineering: Renewable Sources, No. 181, vol. 74, p. 105-110, 1978; and Tang, I. C., Yang, S. T., Okos, M. R., "Acetic Acid Production from Whey Lactose by the Co-culture of *Streptococcus lactis* and *Clostridium formicoaceticum*", Applied Microbiology and Biotechnology, vol. 28, p. 138-143, 1988, which are incorporated herein by reference in their entirety) have been conducted to examine the effects of pH and acetate levels on both cell growth and acid production. These organism are sensitive to low pH and product inhibition occurs at much lower concentrations than in lactic acid bacteria. Optimal pH is around 7 and maximum acetate tolerance is only about 30 g/l in batch fermentation.

A one or two stage CSTR fermentor design is typically appropriate for the second fermentation step. However, any suitable bioreactor can be used, including batch, fed-batch, cell recycle, and multi-step CSTR. In contrast to the first fermentation step, the acetic acid fermentation is nitrogen limited rather than carbohydrate limited. Yield of acetic acid from lactic acid can be greater than 85% of theoretical.

In one embodiment, the broth from the second fermentation step is prepared for the second part of the current invention which is the chemical conversion. As an example, the broth is clarified with a combination of a centrifuge and a microfilter. The centrifuge removes the bulk of the biomass and reduces the size of the downstream microfilter by reducing its load. The microfilter permeate is sent to a nanofiltration unit. The microfilter acts as a prefilter for the nanofiltration unit. The nanofiltration unit removes proteins, unconverted sugars, etc. which have molecular weights above about 300. The nanofiltration unit removes the bulk of the impurities in the acetate broth and produces a water white permeate that can be sent to downstream processes.

The concentrates from the centrifuge, microfilter and nanofilter may be processed to recover values useful in the single cell protein or recycled to one of the fermentation steps. Alternatively, they may be disposed of in any acceptable manner such as composting or incineration.

Although a preferred embodiment of the current invention utilizes two fermentation steps and the production of single cell protein, this is not required in the most general case. A suitable medium for the acetic acid fermentation alone may be provided. Although single cell protein may not be produced, the increased yield form the carbohydrate source will still provide an important advantage for the current invention.

The key feature of the fermentation step is therefore the conversion of carbohydrate from any source into acetic acid.

Acidification and Esterification

In the next step of the invention, the acetic acid or acetate produced in the fermentation is converted to an ester of acetic acid, preferably methyl or ethyl ester and more preferably ethyl ester. Any suitable process that will convert the acetic acid or acetate salt to the ester is acceptable as part of this invention.

Acetic acid is a weak organic acid with pKa=4.76. If the fermentation is conducted at near neutral pH (i.e. pH=7.0), the product of the fermentation will actually largely be an acetate salt rather than the acid. In the fermentation, any suitable base can be used to neutralize the fermentation. The preferred neutralizing agent is $Ca(OH)_2$, which can be supplied by CaO (lime) or calcium carbonate ($CaCO_3$) which can be recycled from later in the process. Other neutralizing agents can be used, such as NaOH or $NH_4OH$, as determined by the conditions required by the fermentation organism. However, even the acetate salt is inhibitory and the maximum concentration of acetate is usually limited to about 5% in the fermentation broth.

Thus, there are two problems in the recovery of acetic acid salts from a solution such as a fermentation broth. The acetate salt must usually be converted to the acid, and the acid must be removed from the dilute solution in water. In addition it is desirable to recycle the base used to neutralize the fermentation to reduce costs and avoid potential environmental impact.

The most typical route is the sequential acidification of the salt to produce acetic acid and then the subsequent recovery of the acid. Even after the salt is converted to a dilute acid solution, there is still the need to recover the product from the water. Many different process approaches have been proposed to recover such dilute solutions. Since acetic acid has a higher boiling point than water, the bulk of the water, about 95% of the broth, must be distilled away from the acetic acid to recover the acid if simple distillation is used. Alternatively, some more complex process may be used to recover the acetic acid, usually in conjunction with solvent extraction. However this line of research, that is, acidification with subsequent recovery from the dilute solution, has not overcome the economic limitations of the acetic acid fermentation process to make it competitive with the synthesis gas based route. Therefore, all industrial acetic acid is currently made from synthesis gas derived from coal, petroleum or natural gas.

A number of methods have been proposed to acidify the acetic acid salt solution. One method is the reaction of the acetate salt with a strong acid such as sulfuric acid to form acetic acid (HAc) and calcium sulfate ($CaSO_4$). The $CaSO_4$ precipitates and is easily separated from the acetic acid solution. However, this method requires the consumption of acid and base and produces a byproduct waste salt that may become an environmental burden. Another method is bipolar electrodialysis that splits the salt into an acid and base (this does not work well with Ca salts, but one could substitute Na in this case). Other routes to produce dilute acetic acid from the salt are well known.

Reaction of a carboxylic acid salt with an amine and $CO_2$ with the precipitation of $CaCO_3$ and the formation of an acid amine complex that can be extracted and thermally regenerated has also been proposed, as shown by U.S. Pat. No. 4,405,717, which is incorporated herein by reference in its entirety.

U.S. Pat. No. 4,282,323, which is incorporated herein by reference in its entirety, discloses a process to acidify acetate salts using $CO_2$ in a number of ways. In the referenced patent the acetic acid formed is removed by a solvent to a separate phase.

Esterification of acetic acid to form ethyl acetate is a well understood reaction:

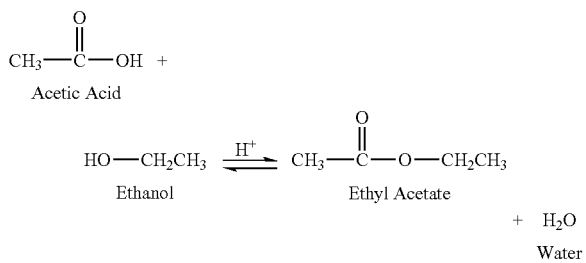

Esterification is typically performed in the liquid phase. The equilibrium constant for this reaction is 4.0 and is nearly independent of temperature. Acid catalysts for the reaction include: strong Bronsted acids such as sulfuric acid and methane sulfonic acid, acidic ion exchange resins, zeolites, and a number of other materials, including carbonic acid formed by the dissolution of $CO_2$ in water. The reaction rate is influenced by the type and concentration of catalyst, the reaction temperature, and the degree of departure from equilibrium.

Alternative routes exist that attempt to avoid the separate acidification and esterification steps. A carboxylic acid salt may be reacted directly with an alcohol such as ethanol to produce the ester directly. An intermediate step may be inserted to convert the Ca salt to an ammonia salt. In this step the dilute $Ca(Ac)_2$ is reacted with NH3 and $CO_2$ to form $NH_4Ac$ and $CaCO_3$ which precipitates. The ammonia salt of acetic acid may then be esterified directly as shown by U.S. Pat. No. 2,565,487, which is incorporated herein by reference in its entirety.

Preferred Approach

The preferred approach is to combine chemical and phase change operations into a new efficient process to directly produce a volatile ester of acetic acid and distill the ester away from the broth.

The three parts are:

1) Acidification of the fermentation broth with $CO_2$ at low or nearly atmospheric pressure to produce acetic acid and precipitate $CaCO_3$ which can be recycled directly to the fermentation as the base;

2) Simultaneous esterification of the formed acetic acid with an alcohol, such as methyl or ethyl alcohol, to form a volatile ester, and 3) Reactive distillation to push the acidification and esterification equilibria to high conversion.

Since esterification is an equilibrium reaction, high conversion can be obtained by driving the reaction to the right with continuous removal of one or more products. Reactive distillation similar to that developed by Chronopol for lactide synthesis (See U.S. Pat. No. 5,750,732, which is incorporated herein by reference in its entirety) and by Eastman Chemical for methyl acetate production (see U.S. Pat. Nos. 4,939,294 and 4,435,595 and Agreda, V. H., Partin, L. R., Heise, W. H., "High-Purity Methyl Acetate Via Reactive Distillation", Chemical Engineering Progress, p. 40-46, February 1990, which are incorporated herein by reference in their entirety) is an economically attractive method. U.S. Pat. No. 5,599,976, which is incorporated herein by reference in its entirety, discloses the conversion of very dilute acetic acid to the ester in a continuous reactive distillation process. Xu and Chaung (Xu, Z. P, Chuang, K. T., "Kinetics of Acetic Acid Esterification over Ion Exchange Catalysts", Can. J. Chem. Eng., pp. 493-500, Vol. 74, 1996) show that reactive distillation to produce the ester of acetic acid from dilute solution is the preferred method to remove acetic acid from very dilute solutions, as are produced in the current invention. In this concept, the acetic acid flows in a counter current fashion to the esterifying ethanol in a distillation column. In the current invention, ethyl acetate is more volatile than acetic acid so the ethyl acetate is distilled away from the liquid mixture and the esterification reaction is pushed to the right, thus enabling high conversions in a single vessel. The process proposed here goes beyond these examples in that its combines simultaneous acidification with the reactive distillation esterification. All of the cited processes start with acetic acid (or lactic acid in the Chronopol case) and not a salt.

The net effect of the reactive distillation process, the preferred route, is to remove the acetic acid from the dilute solution without vaporizing the water which forms the bulk of the stream.

In addition, the use of $CO_2$ as the preferred acidifying agent with the precipitation of $CaCO_3$ allows the recycle of the neutralizing agent to the fermentation without the consumption of chemicals. The $CaCO_3$ can be used directly in the fermentation or can be converted first to CaO by calcination.

Figure 5:
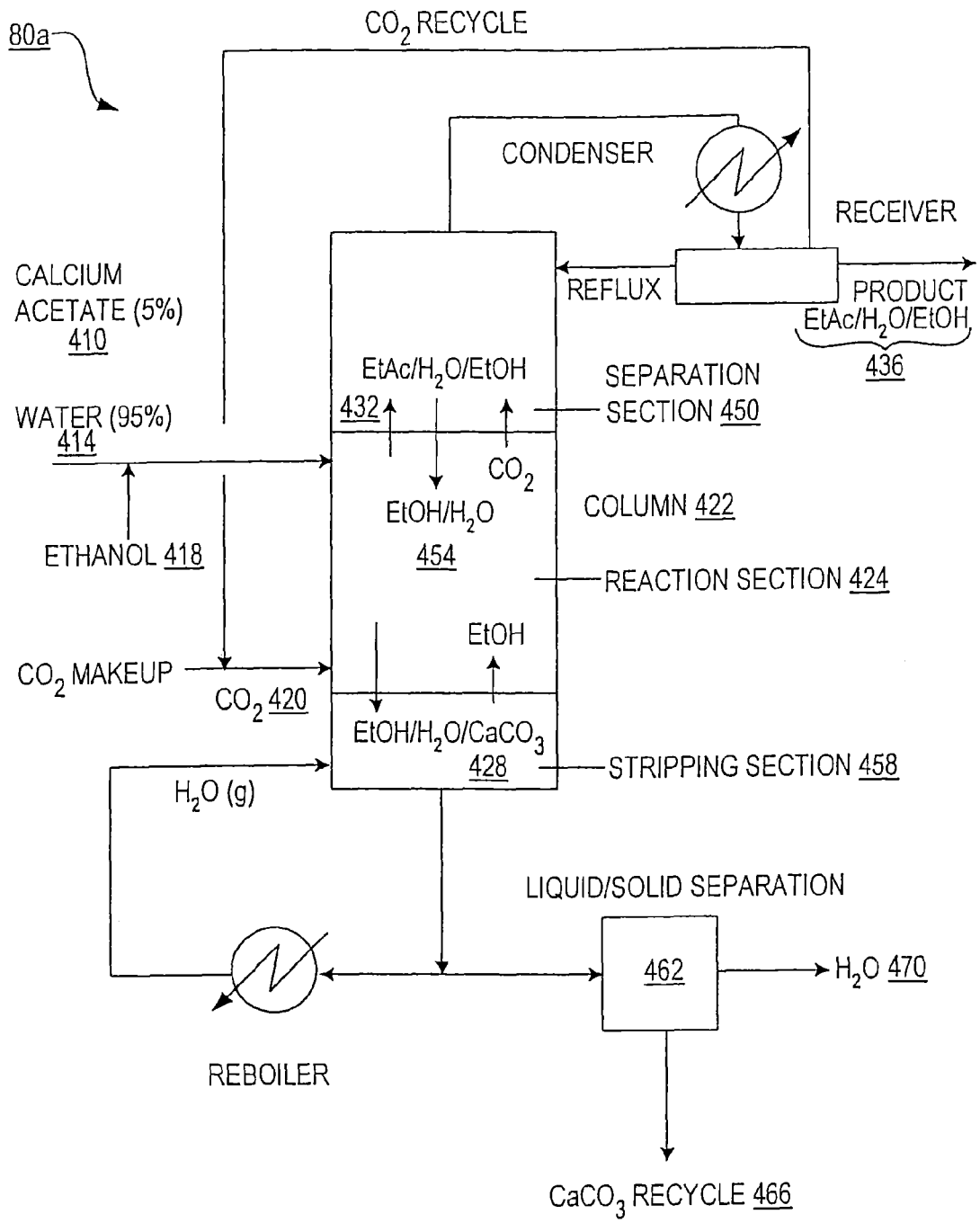
FIG. 5 illustrates one embodiment of reactive distillation.

The reactive distillation process is shown in FIG. 5.

Reaction section: The raw material, a dilute (5%) solution of calcium acetate 410 ($Ca(Ac)_2$) in water 414 is mixed with ethanol 418 and fed to the column 422 at the top of the reaction section 424. $CO_2$ 420 is fed to the column 422 at the bottom of the reaction section 424. The simultaneous reaction of $CO_2$ 420 with $Ca(Ac)_2$ 410 and ethanol 418 takes place in the reaction zone 424 in the center section of the column 422 with the formation of $CaCO_3$ 428 and ethyl acetate (EtAc) 432.

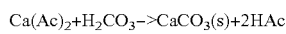

The most volatile component in the reaction mixture is the ethyl acetate/water/ethanol azeotrope 436. The azeotrope composition is 82.6% ethyl acetate, 9% water and 8.4% ethanol and has a normal boiling point of 70.2° C. The azeotrope 436 is removed from the reaction mixture by vaporization along with some EtOH and water. The bottom product from the reaction zone is a water and ethanol solution containing the suspended $CaCO_3$ flowing to the stripping section.

Separation Section: In the upper separation zone 450 the azeotrope is separated from the ethanol and water also vaporized from the reaction mixture. The ethanol water mixture 454 is recycled to the reaction zone 424 and the overhead product is the azeotrope 436. The $CO_2$ is separated from the overhead condensate and recycled to the column with makeup $CO_2$. The azeotrope can be broken by the addition of water, which causes a phase separation, with the water and ethanol rich phase returned to the appropriate point in the reactive distillation column (not shown).

Stripping Section: Since excess ethanol is used to favor the forward esterification reaction in the reaction section, the stripping section 458 returns the excess ethanol to the reaction zone. In the stripping section 458, the ethanol is removed from the $CaCO_3$-containing water stream which is discharged from the column 422 and separated by a simple liquid/solid separation 462, such as centrifugation or filtration, into the solid base 466 for recycle and water 470.

The net effect of the reactive distillation process is to recover the acetic acid from the dilute salt solution thereby producing a relatively concentrated product stream at the top and without vaporizing the water that forms the bulk of the stream. The integration of the three sections reduces the energy requirement. The simultaneous removal of the product ester shifts the esterification equilibrium and leads to higher conversion in a short time.

It is unusual to handle precipitates in a distillation system. However, in this case the precipitation reaction occurs in the bulk phase and is not due to the concentration of the solution at a heat transfer surface, a common type of fouling. Ethanol beer stills in the corn dry milling ethanol industry typically handle solids loading in the stripping section through the use of trays with simple construction and large openings. Alternatively, it would be possible to operate the reaction section in other configurations, such as a series of stirred tanks with a common vapor manifold, to simulate the column reaction section.

The successful development of a low cost, low energy, integrated acidification, esterification and purification process for ethyl acetate would potentially allow the economic production on an industrial scale of major chemicals from renewable resources, which are now produced from non-renewable resources.

One major benefit of using renewable resources is the reduction of $CO_2$ production with the replacement of fossil raw materials. There would be a benefit to the U.S. economy from the replacement of imported petroleum with domestic renewable resources. The use of agricultural commodities to produce chemicals and liquid fuels without subsidy has important benefits to the farm community in terms of product demand and stable markets and reduces the cost of U.S. government subsidies.

Hydrogenation

The third major step in the invention is the conversion of the ester of acetic acid into two alcohols by hydrogenation. The hydrogenation of esters to produce alcohols is a well-known reaction.

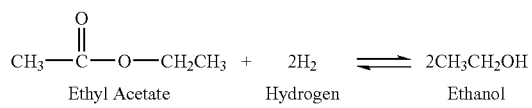

U.S. Pat. Nos. 2,782,243, 4,113,662, 4,454,358, and 4,497,967, which are incorporated herein by reference in their entirety, disclose processes for the hydrogenation of esters of acetic acid to ethanol.

For the particular case at hand, hydrogenation can be performed in either the liquid phase or the gas phase. Any suitable hydrogenation process can be used. This reaction is also an equilibrium reaction. The reaction can be driven to the right by using high partial pressures of hydrogen. Typical reaction conditions are 150-250° C. and 500-3000 psi depending upon the desired conversion and selectivity. The reaction can be catalyzed by any suitable hydrogenation catalysts, such as copper chromite, nickel, Raney nickel, ruthenium, and platinum. A copper chromite, nickel, or Raney nickel catalyst is preferred for the hydrogenation since these catalysts are not poisoned by water. In the liquid phase process, an alcohol such as ethanol is a good solvent.

In the gas phase process, the ethyl acetate feed is vaporized and fed to the hydrogenation reactor with an excess of hydrogen. After passing through the bed, the vapors are cooled and flashed into a low pressure knockout drum. The hydrogen rich vapor phase is recycled back to the reactor. The liquid phase is distilled to remove residual water and unreacted ethyl acetate. The water is not made by the hydrogenation chemistry; its source is the liquid-liquid equilibrium level present in the upstream reflux drum of the reactive distillation column.

Another distillation column may be needed as a final polishing step, depending upon the nature and quantities of side products from the esterification and hydrogenation units.

The preferred ester is ethyl acetate, as it avoids the introduction of a second compound into the process which must be purified away from the product stream.

The water stripper collects water streams from the acidification, esterification, and hydrogenation units. The water is steam stripped to recover solvent values, then the water is sent to final treatment and discharge or recycled to the fermentation section.

Many potential sources of hydrogen for use in the present invention exist. Any suitable hydrogen source can be used that produces hydrogen of sufficient purity for the hydrogenation reaction and that will not poison the catalyst. Raw materials for hydrogen production include water from which hydrogen can be produced by electrolysis. Many fossil and renewable organic feedstocks can also be used. If a fossil feedstock is used, such as methane from natural gas, some $CO_2$ will be produced along with the hydrogen. However, if a renewable feedstock is used then the $CO_2$ production will be neutral to the environment. For example, feedstocks which contain carbon and hydrogen at the molecular level can be used to produce hydrogen. Wood chips, sawdust, municipal wastes, recycled paper, wastes from the pulp and paper industry, solid agricultural wastes from animal and/or crop production are all examples of renewable feedstocks that can be used for hydrogen production, e.g., using gasification technology.

Steam reforming of methane to produce hydrogen is a well know process. Natural gas and water are reacted in a steam reformer to form hydrogen and carbon dioxide. Other methods to produce hydrogen (partial oxidation of hydrocarbons, partial oxidation of coal, water electrolysis, etc.) could also be used. Where pure oxygen is available, such as in a fenceline operation with an air separations plant, the partial oxidation processes can be economically viable. Where inexpensive sources of electricity are available, electrolysis can be viable.

Another advantage of the current invention, compared to prior art technology for ethanol production, is the heat balance in the process. In the current invention, if hydrogen is made by steam reforming on site, excess heat is available at high temperature and in an integrated plant due to the hydrogenation reaction of the ester being a highly exothermic process. Therefore, the overall process is highly energy efficient. In addition, none of the carbohydrate raw material is wasted as $CO_2$ with the attendant generation of heat, which must be wasted to cooling water.

While various embodiments of the present invention have been described in detail, it is apparent that modifications and adaptations of those embodiments will occur to those skilled in the art. However, it is to be expressly understood that such modifications and adaptations are within the spirit and scope of the present invention.

What is claimed is:

1. A process for upgrading the unfermented fraction of corn from a yeast fermentation based corn dry milling ethanol process, comprising:
   a. hydrolyzing an unfermented fraction of corn from a yeast fermentation based corn dry milling ethanol process;
   b. separating the hydrolyzed unfermented fraction into a solids fraction and a liquid hydrolyzate;
   c. culturing a microorganism in the liquid hydrolyzate; and
   d. wherein the solids fraction has an increased protein content compared to the unfermented fraction.

2. The process, as claimed in claim 1, wherein the protein content of the solids fraction is at least about 35% protein on a dry weight basis.

3. The process, as claimed in claim 1, wherein the protein content of the solids fraction is at least about 45% protein on a dry weight basis.

4. The process, as claimed in claim 1, wherein the protein content of the solids fraction is at least about 50% protein on a dry weight basis.

5. The process, as claimed in claim 1, wherein the step of hydrolyzing the unfermented fraction comprises enzymatic hydrolysis.

6. The process, as claimed in claim 1, wherein the step of hydrolyzing comprises contacting the unfermented fraction with a xylanase.

7. The process, as claimed in claim 1, wherein the step of hydrolyzing comprises contacting the unfermented fraction with a cellulase.

8. The process, as claimed in claim 1, further comprising the step of drying the solids fraction.

9. The process, as claimed in claim 1, wherein the microorganism is homofermentative.

10. The process, as claimed in claim 1, wherein the step of culturing produces acetate, acetic acid, or mixtures thereof.

11. The process, as claimed in claim 10, further comprising chemically converting the acetate, acetic acid or mixtures thereof to an ester of acetic acid.

12. The process, as claimed in claim 1, wherein the unfermented fraction comprises a bottoms fraction produced by distilling ethanol from the yeast fermentation.

13. A process for upgrading the unfermented fraction of corn from a yeast fermentation based corn dry milling ethanol process, comprising:
   a. hydrolyzing an unfermented fraction of corn from a yeast fermentation based corn dry milling ethanol process, wherein the step of hydrolyzing comprises enzymatic hydrolysis;
   b. separating the hydrolyzed unfermented fraction into a solids fraction, comprising at least about 35% protein on a dry weight basis and a liquid hydrolyzate;
   c. culturing a microorganism in the liquid hydrolyzate; and
   d. wherein the solids fraction has an increased protein content compared to the unfermented fraction.

14. The process, as claimed in claim 13, wherein the protein of the solids fraction is at least about 45% protein on a dry weight basis.

15. The process, as claimed in claim 13, wherein the protein of the solids fraction is at least about 50% protein on a dry weight basis.

16. The process, as claimed in claim 13, wherein the step of hydrolyzing comprises contacting the unfermented fraction with a xylanase.

17. The process, as claimed in claim 13, wherein the step of hydrolyzing comprises contacting the unfermented fraction with a cellulase.

18. The process, as claimed in claim 13, further comprising the step of drying the solids fraction.

19. The process, as claimed in claim 13, wherein the microorganism is homofermentative.

20. The process, as claimed in claim 13, wherein the step of culturing produces acetate, acetic acid, or mixtures thereof.

21. The process, as claimed in claim 20, further comprising chemically converting the acetate, acetic acid or mixtures thereof to an ester of acetic acid.

22. The process, as claimed in claim 13, wherein the unfermented fraction comprises a bottoms fraction produced by distilling ethanol from the yeast fermentation.

* * * * *